United States Patent [19]

DeCrosta et al.

[11] Patent Number: 4,575,539
[45] Date of Patent: Mar. 11, 1986

[54] DRUG DELIVERY SYSTEMS INCLUDING NOVEL INTERPENETRATING POLYMER NETWORKS AND METHOD

[75] Inventors: Mark T. DeCrosta, Plainsboro; Nemichand B. Jain, Monmouth Junction; Edward M. Rudnic, Kendall Park, all of N.J.

[73] Assignee: E. R. Squibb & Sons, Inc., Princeton, N.J.

[21] Appl. No.: 740,689

[22] Filed: Jun. 3, 1985

[51] Int. Cl.$^4$ .............................................. C08L 33/14
[52] U.S. Cl. ...................................... 525/283; 424/81; 525/293; 525/301; 525/303
[58] Field of Search ............... 525/283, 293, 301, 303; 524/516, 522, 523, 916

[56] References Cited

U.S. PATENT DOCUMENTS

| | | | |
|---|---|---|---|
| 3,639,524 | 2/1972 | Seiderman | 525/283 |
| 3,721,657 | 3/1973 | Seiderman | 525/283 |
| 3,839,304 | 10/1974 | Hovey | 525/283 |
| 4,056,496 | 11/1977 | Mancini et al. | 526/230 |
| 4,128,600 | 12/1978 | Skinner | 204/159.19 |
| 4,136,250 | 1/1979 | Mueller et al. | 528/29 |
| 4,224,427 | 9/1980 | Mueller et al. | 526/93 |
| 4,279,795 | 7/1981 | Yamashita | 525/303 |
| 4,320,040 | 3/1982 | Fujita | 524/916 |
| 4,377,661 | 3/1983 | Wright | 525/303 |
| 4,379,864 | 4/1983 | Gallop et al. | 523/106 |
| 4,423,099 | 12/1983 | Mueller et al. | 428/35 |
| 4,424,311 | 1/1984 | Nagaoka | 525/303 |

OTHER PUBLICATIONS

"Drug Release from Hydrogel Devices with Rate-Controlling Barriers", Kim et al., Dept. of Pharmaceutics, U. of Utah, Journal of Membrane Science, 7 (1980), 293-303.

"Gradient-IPN-Modified Hydrogel Beads: Their Synthesis by Diffusion-Polycondensation and Function as Controlled Drug Delivery Agents", Mueller et al., Ciba-Geigy Corp., Journal of Applied Polymer Science, vol. 27, 4043-4064, (1982).

"Preparation and Characterization of Therapeutic Hydrogels as Oral Dosage Forms" Gyselinck et al., Gent, Belg., Acta Pharmaceutica Technologica 29(1), 1983.

"Zero-Order Drug Release from Glassy Hydrogel Beads", Ping I. Lee, Ciba-Geigy.

"Modeling Drug Release from Swellable Systems", Korsmeyer et al., School of Chemical Engineering, Purdue University.

*Primary Examiner*—Paul R. Michl
*Attorney, Agent, or Firm*—Lawrence S. Levinson; Burton Rodney

[57] ABSTRACT

A drug delivery system is provided which is in the form of hydrogel beads employed in a new interpenetrating polymer network which is formed by swelling hydrogel beads with an acrylic swelling agent and reacting the swelling agent with a cross-linking agent. The drug delivery system has superior drug loading capacity and controlled release characteristics.

17 Claims, No Drawings

DRUG DELIVERY SYSTEMS INCLUDING NOVEL INTERPENETRATING POLYMER NETWORKS AND METHOD

FIELD OF THE INVENTION

The present invention relates to a drug delivery system in the form of hydrogel beads employed in a new interpenetrating polymer network wherein one or more acrylate monomers are employed as swelling agents for the hydrogel beads and to a method for forming such interpenetrating polymer network.

BACKGROUND OF THE INVENTION

The use of hydrogels as delivery vehicles for drugs is well documented in U.S. Pat. No. 4,224,427. This patent sets out a detailed discussion of prior art relating to hydrogels and the formation of same.

The particular hydrogel invention disclosed in U.S. Pat. No. 4,224,427 relates to a process for preparing essentially uniform spherical beads of up to 5 mm diameter of a cross-linked, water insoluble hydrogel by suspension polymerization of a water-soluble monoolefin monomer and 0 to 70% of a water-insoluble monoolefinic monomer with a cross-linking agent and a polymerization initiator. The monoolefin monomers contain at least 5% by weight of a hydroxy substituted hydrophilic vinyl monomer. The water-soluble monoolefin monomer can be a hydroxyalkyl ester of acrylic and/or methacrylic acid, e.g., 2-hydroxyethyl, 2- or 3-hydroxypropyl, or 2,3-dihydroxypropyl esters, poly-ethoxylated hydroxyalkyl esters, N-vinyl-2-pyrrolidone or N-methyldiacrylamide. The water-insoluble monomer can be an alkyl acrylate or methacrylate, a vinyl ester of a carboxylic acid, a vinyl alkyl ester, acrylonitrile or styrene. The cross-linking agent is a polyolefinic macromer of molecular weight of 400 to 8000 such as a reaction product of a poly(tetramethylene oxide)glycol with a molecular weight of 600 to 4000, first terminated with toluene-2,4-diisocyanate or isophorone diisocyanate, and then endcapped with a hydroxyalkyl acrylate or methacrylate.

U.S. Pat. No. 4,423,099 to Mueller et al. dated Dec. 27, 1983 discloses hydrogel beads having an intepenetrating membrane incorporated therein. The preferred hydrogel beads are obtained by suspension polymerization of hydroxyalkyl ($C_2$–$C_4$) acrylates or methacrylates, or N-vinyl pyrrolidone containing mixtures, for example, a copolymer of hydroxyethyl methacrylate and N-vinyl pyrrolidone cross-linked with a macromer, being a reaction product of isophorone diisocyanate capped with poly tetramethylene oxide. Other cross-linking agents disclosed are ethylene glycol diacrylate or methacrylate, di-ethylene glycol, polyethylene glycol-diacrylates or methacrylates, acrylate, neopentyl-glycol diacrylate, divinyl benzene, ethylene glycol divinyl ether, di-allyl maleate or fumerate. The hydrogel beads are modified by incorporating therein an interpenetrating membrane which is less permeable than the hydrogel and formed by a condensation polymer which is interwoven with the substrate hydrogel network. This is accomplished by imbibing the hydrogel with a reactant A, followed by immersion of the hydrogel containing such reactant in a medium containing a co-reactant B. Examples of reactants are diisocyanate and water, polyhydric alcohols, poly-primary and poly-secondary amines, aromatic amines, diisocyanates, di-acid chlorides of aliphatic di-carboxylic acids, dialdehydes, anhydrides such as maleic-, succinic-, alkenyl-succinic, phthalic-and tetrahydrophthalic anhydrides. Rapidly occurring reactions disclosed include "dialdehydes+amines to give poly-Schiff bases; diketones or dialdehydes+dihydrazine derivatives to give polyhydrazones; and base of free-radical catalyzed addition of dithiols to olefinic, acrylic or maleic compounds, like ethylene glycol diacrylate or poly(propylene glycol maleate)." It appears that the reaction product obtained is then reacted with a diisocyanate to form the interpenetrating polymer network.

U.S. Pat. No. 4,056,496 to Mancini et al discloses hydrogels which may be used in drug delivery systems formed by the polymerization of a dihydroxyalkyl acrylate or methacrylate, an alkyl acrylate or methacrylate and a cross-linking agent which may be ethylene glycol dimethacrylate (EGDMA) or tetraethylene glycol dimethacrylate, and a minor amount of an epoxidized alkyl acrylate or methacrylate.

U.S. Pat. No. 4,136,250 to Mueller et al discloses a polysiloxane hydrogel formed by copolymerization of a monomer such as 2-hydroxyethyl methacrylate, and a monomer such as N-vinyl pyrrolidone and a siloxane macromer cross-linking agent.

U.S. Pat. No. 4,379,864 to Gallop et al discloses hydrogels formed by polymerization of a dihydroxyalkyl acrylate, a water-insoluble alkyl acrylate or methacrylate, one or more vinylic monomers and/or hydrophilic acrylates including vinyl pyrrolidone and 2-hydroxyethyl methacrylate, and a cross-linking agent which can be ethylene glycol dimethacrylate or triethylene glycol dimethacrylate.

"Preparation and Characterization of Therapeutic Hydrogels as Oral Dosage Forms", Gyselinck et al, Gent, Belg., Acta Pharmaceutica Technologica 29(1) 1983 discloses hydrogel particles based on 2-hydroxyethyl methacrylate (HEMA) cross-linked with glycol dimethacrylate (GDMA), tripropylene glycol diacrylate (TPGDA), tetraethylene glycol diacrylate (TEGDA), pentaerythritol triacrylate (PETA) and hexanedioldiacrylate (HDDA). The hydrogel particles are loaded with procainamide.

"Zero-Order Drug Release from Glassy Hydrogel Beads", Ping I. Lee, Ciba-Geigy, discloses hydrogel beads containing 70% of 2-hydroxyethyl methacrylate (HEMA) and 30% of a polymeric cross-linking agent which is derived from poly-n-butylene oxide (M.W.=2000) by capping with isophorone-diisocyanate followed by reaction with excess HEMA; the beads were synthesized by free-radical suspension polymerization. The hydrogel beads were loaded with oxprenolol, a $\beta$-blocker.

"Modeling Drug Release from Swellable Systems", Korsmeyer et al, School of Chemical Engineering, Purdue University, discloses model systems formed of copolymers of 2-hydroxyethyl methacrylate (HEMA) and N-vinyl pyrrolidone (NVP) which were bulk-polymerized in polyethylene vials and then lathe cut into disks of desired thickness.

"Drug Release from Hydrogel Devices with Rate-Controlling Barriers", Kim et al., Dept of Pharmaceutics, U. of Utah, Journal of Membrane Science, 7(1980) 293–303 discloses progesterone-dispersed monolithic devices prepared from either polyhydroxyethyl methacrylate (HEMA) or a copolymer of HEMA and methoxyethoxyethyl methacrylate (MEEMA) which were soaked in an ethanol solution of ethylene glycol dimethacrylate (EGDMA) followed by exposure to UV light to create a cross-linked zone at the outer edge.

"Gradient-IPN-Modified Hydrogel Beads: Their Synthesis by Diffusion-Polycondensation and Function as Controlled Drug Delivery Agents", Mueller et al, Ciba-Geigy Corp., Journal of Applied Polymer Science, Vol. 27, 4043–4064 (1982) discloses interpenetrating polymer network (IPN) membranes and gradient-IPN polymers synthesized by immersing cross-linked, α-hydroxyethylmethacrylate copolymer beads which were swollen in polyol in solutions of diisocyanates. Mueller et al form a polyurethane within a preformed water-swellable copolymer matrix: cross-linked polymers based on 2-hydroxyethylmethacrylate and N-vinylpyrrolidone are swollen with a diol or triol and a polyurethane containing IPN is formed by reaction with 2,4,4(2,2,4)-trimethylhexane-1,6-diisocyanate (TMDI).

DESCRIPTION OF THE INVENTION

In accordance with the present invention, a drug delivery system is provided in the form of an interpenetrating polymer network comprised of a water swellable first polymer substrate (which will be in the form of hydrogel beads) interpenetrated by a diffusion rate controlling membrane comprised of a second cross-linked polymer formed of the reaction product of an acrylic swelling agent (for the hydrogel beads), and a cross-linking agent, which reaction product is preferably formed in the presence of a polymerization initiator. A preferred drug delivery system of the invention includes as the acrylic swelling agent methyl methacrylate, acrylic acid or mixtures thereof, as the cross-linking agent ethylene glycol dimethacrylate (EGDMA) and as the polymerization initiator azobisisobutonitrile (AIBN).

Thus, the interpenetrating polymer network of the invention is a combination of two polymers in network form, at least one of which (the cross-linked polymer) is synthesized and/or cross-linked in the immediate presence of the other (hydrogel polymer or beads). An interpenetrating polymer network swells, does not dissolve in solvents and exhibits suppressed creep and flow properties. In the present invention, the cross-linked polymer is synthesized and/or cross-linked in the presence of the hydrogel polymer.

The interpenetrating polymer network of the invention is formed by immersing hydrogel polymer beads in a solution of an acrylic swelling agent and suitable solvent, such as ethanol, methanol, isopropyl alcohol, ethyl acetate or pyridine to form swollen hydrogel beads, then immersing the swollen hydrogel beads in a solution of crosslinking agent, (employing a solvent such as ethanol, methanol or isopropyl alcohol), and heating the mixture to cause reaction of the acrylic swelling agent and cross-linking agent to form cross-linked polymer interpenetrating the hydrogel polymer or beads. The above reaction is preferably carried out in the presence of a polymerization initiator which will preferably be employed in solution containing the cross-linking agent although it may be employed in the solution containing the swelling agent.

In one embodiment, the hydrogel beads may be swelled in a solution of acrylic swelling agent, initiator and cross-linking agent for a period of less than 2 hours and the isolated swollen beads are heated to within the range of from about 60° to about 120° C. to initiate the cross-linking reaction. Additionally, hydrogel beads may be swollen with acrylate and initiator and immersed in solution of cross-linking agent and then heated as described above to cause cross-linking.

In preferred embodiments of the invention, the use of short swelling times, for example, less than about 2 hours, will produce an interpenetrating polymer network (IPN) layer at the surface of the hydrogel polymer.

In addition, in accordance with the present invention, a pharmaceutical composition is provided which is formed of the interpenetrating polymer network of the invention as described above and containing therein a therapeutic drug.

The ability of hydrogel polymers to be loaded with a therapeutic drug and serve as inert carriers for drugs is governed by their degree of swelling in a particular solvent, such as water, and retain a substantial amount of imbibed solvent. Loading is accomplished by swelling these hydrogels in a drug/solvent solution and then driving off the solvent. Drug loading can be increased by lowering the degree of cross-linking and therefore increasing the swelling.

The use of drug loaded hydrogel beads or granules allows delivery of an orally taken drug hours in a reproducible manner. This eliminates wasteful and potentially dangerous peak drug concentrations in the blood, while prolonging the time during which preferred and effective drug levels in the blood are maintained. However, where drugs are released from a monolithic hydrogel matrix by diffusion in an aqueous medium, their release tends to follow first order kinetics, that is the release rate is ordinarily proportional to the drug concentration inside the gel. The release rate is fastest at the very beginning and gradually slows down toward the end. While such a mechanism prolongs the release of an active ingredient and spreads it out long enough to make it useful for instance for orally taken drugs whose metabolic half-life in the body is in the order of several hours, it is not useful for delivering an active substance at a more constant rate, as is necessary for drugs whose metabolic half-life is short.

In such a case, the hydrogel may be interpenetrated by a membrane of lesser permeability. Diffusion through this membrane is the release rate determining step, and the release rate itself is less influenced by the drug concentration in the hydrogel core. Thus, the release rate follows a mechanism close to zero-order.

As indicated, the interpenetrating polymer network of the invention will be formed of hydrogel polymer substrate (which may or may not include drug at this stage) interpenetrated in a gradient substantially normal to the hydrogel substrate by another cross-linked polymer forming a diffusion rate controlling membrane therein.

In forming the interpenetrating polymer network of the invention, the acrylic swelling agent will be employed in a weight ratio to the ethanol or other solvent of within the range of from about 0.01:1 to about 1:1 and preferably from about 0.4:1 to about 0.7:1, and the acrylic swelling agent will be employed in a weight ratio to the cross-linking agent of within the range of from about 1000:1 to about 1:1 and preferably from about 500:1 to about 10:1. The reaction of the swelling agent and the cross-linking agent will preferably be carried out in the presence of a polymerization initiator in which case the polymerization initiator will be employed in a weight ratio to the cross-linking agent of within the range of from about $10^{-5}:1$ to about 0.005:1 and preferably from about 0.00025:1 to about 0.002:1.

Examples of acrylic swelling agents suitable for use herein include but are not limited to acrylic monomers such as acrylic acid, methyl methacrylate, acrylic anhydride, ethylene-vinyl acetate, hydroxyethyl acrylate, methyl acrylate, vinyl pyridine, vinyl chloride, methacrylic acid, acrylamide, hydroxypropyl methacrylate, hydroxyethyl methacrylate, butyl acrylate and the like.

Examples of cross-linking agents suitable for use herein include but are not limited to monomers containing at least two (2) vinyl groups, such as butylene diacrylate, ethylene dimethacrylate, divinyl benzene, ethylene glycol dimethacrylate, tetraethylene glycol dimethacrylate, methyl bisacrylamide as well as other conventional cross-linking agents which will form a cross-linked polymer with the acrylic swelling agent.

Polymerization initiators suitable for use herein include but are not limited to azobisisobutonitrile, peroxide initiators such as benzoyl peroxide, dicumyl peroxide, isopropyl peroxide, acetyl peroxide, t-butyl peroctoate and the like.

The hydrogel polymer or beads which may be employed herein include any of the hydrogels known in the art such as disclosed in U.S. Pat. Nos. 4,423,099, 4,224,427, 4,056,496, 4,136,250, 4,379,864 and the other conventional hydrogels.

A preferred hydrogel polymer, in the form of spherical beads, suitable for use herein will be formed from about 35 to about 90% and preferably from about 40 to about 60% by weight hydroxyethyl methacrylate monomer, from about 1 to about 65% and preferably from about 30 to about 45% by weight N-vinyl pyrrolidone monomer and from about 0.01 to about 20% and preferably from about 2 to about 5% by weight cross-linking agent, the above % by weight being based on the total weight of the polymerization reaction mixture needed to form the hydrogel product.

The hydroxyethyl methacrylate and N-vinyl pyrrolidone are hydrophilic monomers with the latter being more hydrophilic than the former. These monomers when polymerized absorb water and swell. The N-vinyl pyrrolidone also imparts good drug loading and release properties to the copolymer.

The cross-linking agent employed in forming the above preferred hydrogel is characterized by a molecular weight of less than about 1000 and preferably less than about 500, is not sensitive to atmospheric oxidation and has a high reactivity so that polymerization of the above monomers is completed within 24 hours. During polymerization, the cross-linking agent produces a copolymer of the hydroxyethyl methacrylate and N-vinyl pyrrolidone which does not dissolve in the body and passes without change through the gastrointestinal tract.

The preferred hydrogels, preferably in spherical bead form, may be prepared by a simple essentially one step suspension polymerization procedure wherein the liquid monomers (hydroxyethyl methacrylate and N-vinyl pyrrolidone) and crosslinking agent containing polymerizing initiator are dispersed into droplets by suitable stirring upon which bulk polymerization is completed to solid beads or pearls. In forming the hydrogels, an appropriate suspending agent for the monomer droplets during polymerization, such as gelatinous magnesium hydroxide, is prepared, for example, by mixing aqueous NaCl solution, $MgCl_2.6H_2O$ and aqueous NaOH. Other suspending agents which may be employed include nickel chloride.$6H_2O$, zirconium sulfate.$4H_2O$, ferric chloride or aluminum sulfate.$16H_2O$. Monomers, cross-linking agent and polymerizing initiator (for example in an amount within the range of from 0.001 to about 0.5% by weight and preferably from about 0.02 to about 0.1% by weight based on the total weight of the polymerization reaction mixture) are added with stirring. The aqueous:monomer phase ratio employed in the reaction mixture will be at least about 5:1 and preferably within the range of from about 5:1 to about 25:1 to prevent agglomeration. The reaction is allowed to continue with stirring for 0.5 to 48 hours and preferably from about 3 to about 5 hours while heating at about 70° to about 120° C. The particle size of the final hydrogel beads obtained can be controlled by stirring speed, that is, increasing stirring speed reduces particle size. It is preferred to employ stirring speeds of from about 50 to about 500 rpm using an anchor type stirrer which produces an acceptable mean bead size of within the range of from about 250 to about 1200 microns.

The interpenetrating polymer network of the invention may be loaded with therapeutic drug by swelling the interpenetrating polymer network in a saturated drug soution. Usually, if the hydrogel already contains drug, additional loading of the network will not be necessary.

The above preferred hydrogel described above when employed as part of the interpenetrating polymer network of the invention has superior drug loading capacity, improved drug release characteristics, and improved chemical and physical stability.

A wide variety of drugs may be incorporated in the hydrogel polymer which is to be a part of the interpenetrating polymer network of the invention. These include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyridamine and the like, hypotensive agents such as rauwolfia, reserpine and the like, cardioactive agents such as bendroflumethiazide, flumethiazide, chlorothiazide, aminotrate, propranolol, nadolol, procainamide and the like, angiotensin converting enzyme inhibitors such as captopril and enalapril, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, acetominophen, phenylbutazone, propoxyphene, methadone, meperidine and the like, etc. These substances are frequently employed either as the free compound or in a salt form, e.g., acid addition salts, basic salts like alkali metal salts, etc. Other therapeutic agents having the same or different physiological activity can also be employed in the pharmaceutical preparations within the scope of the present invention.

Where the hydrogel is employed in the form of a bead, the interpenetrating polymer network forming the active ingredient rate controlling membrane characteristically exists in the form of a compositional gradient going from high concentration on or near the surface to zero inside the bead, such that the membrane compositional gradient is substantially normal to the hydrogel substrate surface.

This is most easily accomplished by imbibing the hydrogel with the acrylic swelling agent, followed by immersion of the hydrogel containing said swelling agent in a medium containing the cross-linking agent under conditions which allow diffusion of the cross-linking agent into the swelled hydrogel, and promote simultaneously the reaction of the swelling agent and cross-linking agent to form the cross-linked polymer. Synthesized under such conditions, the cross-linked polymer is interwoven with the hydrogel substrate thereby forming a membrane in the form of an interpenetrating polymer network (IPN). The concentration of the interwoven cross-linked polymer and the steepness of its compositional gradient are dependent on the speed and extent of diffusion and on the rate of reaction; when diffusion is much faster than reaction then the IPN will extend deep into the hydrogel, while when the reaction is fast compared to diffusion, the IPN will be concentrated in a more or less narrow volume near the surface of the hydrogel. Where the hydrogel surface is not treated between the swelling step and the immersion step, the hydrogel exhibits a gradient going from high concentration of the cross-linked polymer on the surface to a low concentration and finally zero concentration proceeding to the interior of the hydrogel. If the swelled hydrogel surface is washed with an inert solvent or diluent for the acrylic swelling agent so as to remove a portion of the acrylic swelling agent from the surface of the hydrogel prior to the immersion step, then the gradient can be modified such that there is a low concentration of cross-linked polymer on the surface, increasing to a maximum concentration of interwoven cross-linked polymer then decreasing to zero as one proceeds further towards the interior of the hydrogel bead. In either case, the gradient is substantially normal to the hydrogel substrate surface.

A hydrogel bead interpenetrated with cross-linked polymer and loaded with a soluble drug and immersed in water will swell and therefore change its volume and surface area. At the same time the drug will dissolve and diffuse to the outside while the osmotic pressure gradient will pull more water or gastric fluid inside. After a certain time, when equilibrium swelling has been established, the net flow of water across the interface will be close to zero, although with continuing decline of drug concentration inside the bead of equilibrium water content itself can be expected to change. It is the simultaneous occurrence of these diffusion processes which leads to the substantially zero order unique drug release pattern.

In general, the higher the concentrations of acrylic swelling agents employed the greater the density of the interpenetrating polymer network (IPN) layer in the hydrogel beads. The higher the concentrations of cross-linking agent employed the greater the cross-link density of the IPN layer and the more drug release from the hydrogel beads is retarded.

Where the hydrogel is in the form of a sheet or a bag, one may form the membrane by treating one surface by the swelling procedure, optionally followed by the washing process, and then treating the same surface by immersion of the hydrogel containing the swelling agent therein into the cross-linking medium. Again the interwoven membrane is present as a gradient normal to the surface of the sheet or bag. The hydrogel inbibed with the swelling agent does not have to contain this agent uniformly distributed, but it is enough to swell only the surface region.

Alternatively, the opposite sides of the hydrogel sheet or bag may be treated with swelling and cross-linking agent, respectively. Thus, for example, the interior of a hydrogel bag may be filled with a liquid medium containing swelling agent and the bag placed in a medium containing the cross-linking agent. As the swelling agent diffuses from oposite sides of the bag, the cross-linked polymer is formed as an interwoven network at an interface inside the polymer substrate. The bag is then removed from the respective media and washed to obtain a hydrogel bag containing a less permeable membrane parallel to the respective surfaces of the bag in a gradient which is low or zero at the surfaces, going to a high concentration in the interior, and is again normal to the bag surfaces. Like sheets and bags, tubes and hollow fibers are equally well suited to be modified by IPN according to this invention. The active ingredients may be placed therein and the ends closed; sheets may be used to close off an active ingredient containing reservoir.

In a preferred method for forming the interpenetrating polymer network of the invention, hydrogel beads, such as formed from hydroxyethyl-N-vinyl pyrrolidone-tetraethylene glycol dimethacrylate, are swollen in a solution of acrylic swelling agent (in ethanol or other solvent) which is a comonomer mixture of methyl methacrylateacrylic acid (weight ratio ranging from 2:1 to 12:1). The swelling process may be carried out at room temperature inasmuch as the acrylic comonomers are liquids at room temperature. The beads are allowed to swell for at least about 8 hours to equilibrium after which the swollen beads are removed by filtration. The filtered beads are then immersed in a solution of cross-linking agent, preferably ethylene glycol dimethacrylate (EGDMA) and polymerization initiator, preferably azobisisobutonitrile (AIBN) in ethanol or other solvent, employing a weight ratio of cross-linking agent to acrylic swelling agent of within the range of from about 1:1 to about 0.001:1 and a weight ratio of cross-linking agent to polymerization initiator of within the range of from about 0.001:1 to about 0.005:1. The filtered swollen beads are allowed to react at a temperature of within the range of from about 70° C. to about 120° C. for about 3 to about 7 hours. Thereafter, the interpenetrating polymer network (IPN) beads are extracted with ethanol or other solvent, and the beads are filtered and dried. The beads may then be loaded with drug by swelling in a drug/ethanol (or other solvent) solution. The beads are then dried and ready for use.

The following Examples represent preferred embodiments of the present invention. Unless otherwise indicated, all temperatures are expressed in degrees Centigrade.

EXAMPLE 1

Preparation of Hydrogel Beads

To a liter resin flask containing four glass blown baffles and equipped with a four angle turbine impeller, reflux condenser and thermometer, were charged 450 g of a 20% by weight aqueous NaCl solution, followed by 28.75 g $MgCl_2.6H_2O$ and 153.75 ml of a 1N NaOH solution. The mixture was vigorously stirred at 400 rpm. After the addition of the NaOH, the stirring speed was reduced to 125 rpm. Stirring was continued for about 60 minutes until a gelatinous precipitate formed which acts as the suspending agent for the monomer droplets during the polymerization discussed below.

Next, were added, with stirring, hydroxyethyl methacrylate (HEMA) (67.5 ml) and N-vinyl pyrrolidone (NVP) (52.5 ml), tetraethylene glycol. dimethacrylate (TEDGMA) (3.567 ml, M.W. less than <1000) and as a polymerization initiator t-butyl peroctoate (61.75 microliters, 0.05%). The aqueous to monomer phase ratio was 5:1. The reaction was run for 3 hours at 80° and then the temperature was increased to 100° for 1 hour.

Hydrogel beads of 450 microns (−30/+50 mesh) mean particle size were produced. The so-formed hydrogel beads were found to have good chemical and physical stability and superior drug loading capacity.

Preparation of Interpenetrating Polymer Network (IPN)

The hydrogel beads (5 g) synthesized by suspension polymerization as described above were swollen in a 90:10 solution of methyl methacrylateacrylic acid (100 g) in ethanol plus 1.64 g AIBN at room temperature for 18 hours until equilibrium was reached. The swollen beads were then filtered. The swollen hydrogel beads were then suspended in a solution of 2.9 g of ethylene glycol dimethacrylate (EGDMA, cross-linking agent), in 100 g of ethanol and stirred in a flask equipped with reflux-condenser and nitrogen sparge for 3 hours at 70° C. upon which radical chain polymerization was complete.

The so-formed interpenetrating polymer network (IPN) beads were filtered and extracted with ethanol to remove linear polymethyl methacrylate-acrylic acid. The beads were then dried at 50° C. in vacuo. The dry beads were then added to a saturated solution of captopril (22.5 g) in ethanol (50 g) which caused the IPN beads to swell and absorb 30% captopril based on the weight of the beads.

The IPN beads loaded with captopril were found to be a controlled release delivery system.

EXAMPLE 2

IPN hydrogel beads in accordance with the present invention were formed employing the procedure as outlined in Example 1 except that the azobisisobutylnitrile (AIBN) (1.64 mg) initiator was employed with the solution of the acrylic swelling agent.

EXAMPLE 3

IPN hydrogel beads in accordance with the present invention were formed employing the procedure as outlined in Example 1 except that ethylene glycol dimethacrylate (EGDMA) and the initiator were employed with the solution of swelling agent.

EXAMPLE 4

Hydrogel beads (5 g) (prepared as described in Example 1) were immersed in a solution containing 100 g ethanol, 1.64 g azobisisobutonitrile (AIBN), methyl methacrylate-acrylic acid comonomer (100 g) and 2.9 g ethylene glycol dimethacrylate (EGDMA) for 90 minutes until swollen to a desired degree. The swollen beads were removed from the solution and polymerized by heating through refluxing hexane vapor. The so-formed IPN beads were then loaded with captopril to form a controlled release dosage form of captopril.

What is claimed is:

1. An interpenetrating polymer network drug delivery system comprised of a hydrogel polymer interpendetrated by and interwoven with a diffusion rate controlling membrane formed of a cross-linked polymer consisting essentially of the reaction product of a swelling agent which is acrylic acid, methyl methacrylate, acrylic anhydride, ethylene-vinyl acetate, hydroxyehtyl acrylate, methyl acrylate, vinyl pryidine, vinyl chloride, methacrylic acid, acrylamide, hydroxy propyl methacrylate, hydroxyethyl methacrylate, butyl acrylate or mixtures thereof and a cross-linking agent which is butylene diacrylate, ethylene diemthacrylate, divinyl benzene, ethylene glycol dimethacrylate, tetraethylene glycol dimethacrylate or methyl bisacrylamide.

2. The drug delivery system as defined in claim 1 wherein said reaction product is formed in the presence of a polymerization initiator.

3. The drug delivery system as defined in claim 1 wherein the swelling agent is employed in a weight ratio to the cross-linking agent of within the range of from about 1:1 to about 1000:1.

4. The drug delivery system as defined in claim 2 wherein the polymerization initiator is employed in a weight ratio to the cross-linking agent of within the range of from about 0.00001:1 to about 0.005:1.

5. The drug delivery system as defined in claim 1 wherein the swelling agent is acrylic acid, methyl methacrylate, or mixtures thereof.

6. The drug delivery system as defined in claim 7 wherein the swelling agent is a mixture of acrylic acid and methyl methacrylate.

7. The drug delivery system as defined in claim 6 wherien the acrylic acid is present in a weight ratio to the methyl methacrylate of within the range of from about 5% to about 50%.

8. The drug delivery system as defined in claim 1 wherein said cross-linking agent is butylene diacrylate, ethylene dimethacrylate, ethylene glycol dimethacrylate, or tetraethylene glycol dimethacylate.

9. The drug delivery system as defined in claim 8 wherein the cross-linking agent is ethylene glycol dimethacrylate.

10. The drug delivery system as defined in claim 2 wherein the polymerization initiator is azobisisobutonitrile, benzoyl peroxide, dicumyl peroxide, t-butyl peroctoate, isopropyl peroxide, acetyl peroxide or ethyl peroxide.

11. The drug delivery system as defined in claim 2 wherein the swelling agent is a mixture of methyl methacrylate and acrylic acid, the cross-linking agent is ethylene glycol dimethacrylate and the polymerization initiator is azobisisobutonitrile.

12. The drug delivery system as defined in claim 1 wherein the hydrogel polymer is comprised of the cross-linked copolymerization product of from about 35 to about 90% by weight of said hydrogel of hydroxyethyl methacrylate monomer, from about 1 to about 65% by weight of said hydrogel of N-vinyl pyrrolidone monomer, and from about 0.01 to about 20% by weight of said hydrogel of a cross-linking agent selected from the group consisting of tetraethylene glycol dimethacrylate, ethylene glycol dimethacrylate, divinyl glycol, divinyl benzene and ethylene dimethacrylate.

13. The drug delivery system as defined in claim 12 as defined in claim 1 wherein the cross-linking agent is tetraethylene glycol dimethacrylate.

14. The drug delivery system as defined in claim 12 wherein the hydroxyethyl methacrylate is employed in a weight ratio to the cross-linking agent of within the range of from about 90:1 to about 15:1 and the N-vinyl pyrrolidone is employed in a weight ratio to the cross-linking agent of within the range of from about 1000:1 to about 4:1.

15. The gel as defined in claim 1 in the form of a bead.

16. A process for preparing an interpentrating polymer network as defined in claim 1 which comprises immersing said hydrogel polymer in a solution of swelling agent until said hydrogel polymer absorbs said swelling agent and swells to a desired degree to form swollen hydrogel polymer, treating said swollen polymer with a solution of cross-linking agent, optionally in the presence of a polymerization initiator, and heating the mixture to form cross-linked polymer interpenetrating said hydrogen polymer.

17. The process as defined in claim 16 wherein the polymerization is carried out at a temperature within the range of from about 50° to about 150° C. for 0.5 to about 48 hours.

* * * * *

UNITED STATES PATENT AND TRADEMARK OFFICE
CERTIFICATE OF CORRECTION

PATENT NO.   :   4,575,539

DATED        :   March 11, 1986

INVENTOR(S)  :   Mark T. DeCrosta et al.

It is certified that error appears in the above-identified patent and that said Letters Patent is hereby corrected as shown below:

Column 4, line 24, after "drug" and before "hours" insert
  --into the bloodstream to spread out over several--.
Column 10, line 20, "hydroxyehtyl" should read
  --hydroxyethyl--.
Column 10, line 25, "diemthacrylate" should read
  --dimethacrylate--.

Signed and Sealed this

Twenty-eighth Day of October, 1986

[SEAL]

Attest:

DONALD J. QUIGG

Attesting Officer      Commissioner of Patents and Trademarks